United States Patent [19]
Hotchkiss et al.

[11] Patent Number: 5,100,403
[45] Date of Patent: Mar. 31, 1992

[54] DYNAMIC ELBOW SUPPORT

[75] Inventors: Robert N. Hotchkiss, San Antonio, Tex.; Kenneth W. Hotchkiss, Golden; Arthur Woodward, Lakewood, both of Colo.

[73] Assignee: Smith & Nephew Richards, Inc.

[21] Appl. No.: 535,170

[22] Filed: Jun. 8, 1990

[51] Int. Cl.⁵ .............................................. A61F 5/00
[52] U.S. Cl. ........................................ 606/56; 606/57; 128/25 R; 128/56; 602/16; 602/20
[58] Field of Search ............... 128/25 R, 26, 77, 83, 128/85, 49, 52, 56, 67; 606/56, 57, 58, 66, 90, 105

[56] References Cited

U.S. PATENT DOCUMENTS

| | | | |
|---|---|---|---|
| 3,976,061 | 8/1976 | Volkov et al. | 606/56 |
| 3,985,127 | 10/1976 | Volkov et al. | 606/56 |
| 4,100,919 | 7/1978 | Oganesyan et al. | 606/56 |
| 4,338,927 | 7/1982 | Volkov et al. | 606/56 |
| 4,643,177 | 2/1987 | Sheppard et al. | |
| 4,801,138 | 1/1989 | Airy et al. | 128/25 R X |

FOREIGN PATENT DOCUMENTS

| | | | |
|---|---|---|---|
| 0644469 | 1/1979 | U.S.S.R. | 128/25 R |
| 0959769 | 9/1982 | U.S.S.R. | 606/56 |

Primary Examiner—Robert Bahr
Assistant Examiner—J. Doyle
Attorney, Agent, or Firm—Pravel, Gambrell, Hewitt, Kimball & Krieger

[57] ABSTRACT

A dynamic joint support having proximal and distal support sections and means for rigidly connecting each support section to bone and a pair of hinges connecting each support section to each other and pivoting at the joint to cause movement of the support section and its corresponding attached bone through the movements of flexion and extension. The hinge may be driven in its movement by a gear mechanism which may be disengaged by means of a clutch. The dynamic joint support may also include a distraction mechanism for movement of the bones out of contact in the joint, while allowing for an active range of motion at the joint.

5 Claims, 6 Drawing Sheets

DYNAMIC ELBOW SUPPORT

FIELD OF THE INVENTION

The present invention relates generally to the treatment of injuries and contractures of a major skeletal joint such as the elbow and, more particularly, to a dynamic elbow support for allowing the elbow to be flexed and extended either by the patient actively or passively or by a continuous passive motion machine and maintain its alignment for managing contractures.

BACKGROUND OF THE INVENTION

Flexion contractures or a tendency for muscles, tendons or scar tissue to shorten in skeletal joints are common after trauma and represent a major challenge in the care of such injuries. For example, a contracture of 30°–40° in the elbow can severely reduce upper extremity function.

Current approaches to the treatment of elbow trauma have more aggressively sought to prevent contracture and stiffness through movement. Methods of rigid internal fixation with sufficient stability to allow motion within days after injury rather than closed treatment and immobilization in a cast have been developed. In the treatment of dislocations, protected early motion is now begun as soon as the patient is comfortably able to do so.

However, the currently available techniques for the prevention of contracture are not uniformly successful. Early active motion alone can reduce the severity of contracture, but requires the patient's own strength, compliance and constant effort and the proper alignment and tracking of elbow cannot be insured. Passive stretching by a therapist can be done on a very limited basis and is applied slowly, but such therapy risks the formation of heterotopic bone and myositis ossifications. Dynamic splints may be used, but these require pressure on the sometimes sensitive or injured soft tissues of the arm and forearm, and may not be possible, i.e. burn injury, or may reduce patient compliance. Examples of such splinting devices include a turnbuckle orthosis or cast, reverse dynamic sling, polycentric cast brace hinges, or a hinged orthoses with rubber band traction.

Continuous passive motion (CPM) devices have been developed which provide early motion gains, but these devices do not normally allow the joint to come to the extremes of motion which are the areas of greatest need. Further, these devices are not designed to insure accurate tracking or stability of the elbow joint, but instead move the wrist relative to the shoulder or the humerus. These devices also rely on direct pressure on the soft tissues and skin, and thus are subject to the same limitations as the external splints discussed above.

Flexion-extension hinge distractors are hinged external fixators which are designed to hold the joints such as the elbow in distraction while permitting an active range of motion. These include the Volkov elbow hinge-distractor and the Deland and Walker hinge distractor. These devices require the placement of a pin or wire into or in close proximity to the kinematic axis of the elbow, with the pin acting as the mechanical axis of the device. Because these devices are difficult to align over the axis of rotation, pin tracking problems can occur. Furthermore, the mechanical axis cannot be realigned without reinsertion of the pin. In addition, these systems do not permit passive driving of the joint through a range of motion.

An additional problem associated with the flexion-fixation hinge distractors is the placement of pins in close proximity to the joint. Because of the movement of skin over and relative to underlying bone, movement of the skin in this area with normal flexion and extension of the elbow in relation to a stationary pin can cause skin irritation and lead to infection. Such placement of the pins may also interfere with the treatment of a fracture by internal fixation.

Because of limitations with the currently available methods to prevent or treat joint injuries, patients often require surgical soft tissue release to improve the range of motion. Surgical release of contracture must be followed by many months of intensive therapy and splinting to maintain the gains in motion. Such maintenance is not uniformly successful, as the splinting and traditional therapies applied suffer from the same limitations as discussed above. Moreover, oftentimes the cost of surgery and therapy, as well as the costs in time, lost wages and rehabilitation can be significant.

SUMMARY OF THE INVENTION

In order to solve the problems described above, a dynamic joint support is provided which includes proximal and distal external bracing sections, respectively connected to the upper arm and forearm on opposite sides of a joint. The bracing sections are rigidly connected to their respective limbs through support rings which encircle at least part of the limb and are connected to internal bone through wires or pins.

A hinge connects the bracing sections to each other in the vicinity of the joint so that the hinge can pivot at the joint when the limbs are moved through flexion or extension. The hinge includes an X-ray transparent material at the pivot point with target cross hairs so the axis of the hinge can be aligned with the axis of the joint.

Appropriate adjusters are included with the external bracing sections for adjusting the length and orientation of the bracing sections relative to their respective limbs and to the hinge for aligning the bracing sections relative to the joint. This alignment permits accurate placement of the axis of rotation of the device to recreate the normal kinematics of the joint.

The hinge also includes a gear mechanism which can be used for moving the bracing sections and consequently their respective limbs relative to each other through the application of external force to the gear mechanism. The external force can be applied through a manually operated crank or a motor in order to stretch soft tissue surrounding the joint and thereby address a joint contracture. A clutch is also provided so that the gear mechanism can be disengaged for allowing the limbs to move freely under the patient's own muscle force through flexion and extension.

An adjustment mechanism can also be provided for placing the joint in distraction and maintaining its alignment in that position while the skeletal elements are moved through flexion and extension.

By providing the mechanism as described, contractures in the vicinity of a joint, such as an elbow, can be prevented through active or passive movement of the limb through the joint. Continuous passive motion can be applied to the joint with proper tracking and concomitant stability that comes from maintaining the skeletal elements in proper orientation relative to each other while they are being moved.

Further, the subject dynamic joint support also allows the joint to be held in distraction while permitting an active range of motion. All of the above can be performed without pins or wires in close proximity to the joint which eliminates skin irritation because there will be less skin motion relative to the underlying bone during movement of the limbs. Further, the location of the pins is discretionary with the physician so that pins can be placed away from a fracture and not interfere with the healing process of a fracture in the vicinity of the joint. In addition, the apparatus may be designed to permit unrestricted access to the anterior portion of the joint for medical and surgical procedures.

BRIEF DESCRIPTION OF THE DRAWINGS

A better understanding of the invention can be obtained from the detailed description of a preferred embodiment set forth below, when considered in conjunction with the appended drawings, in which.

DETAILED DESCRIPTION OF THE INVENTION

Figure 1:
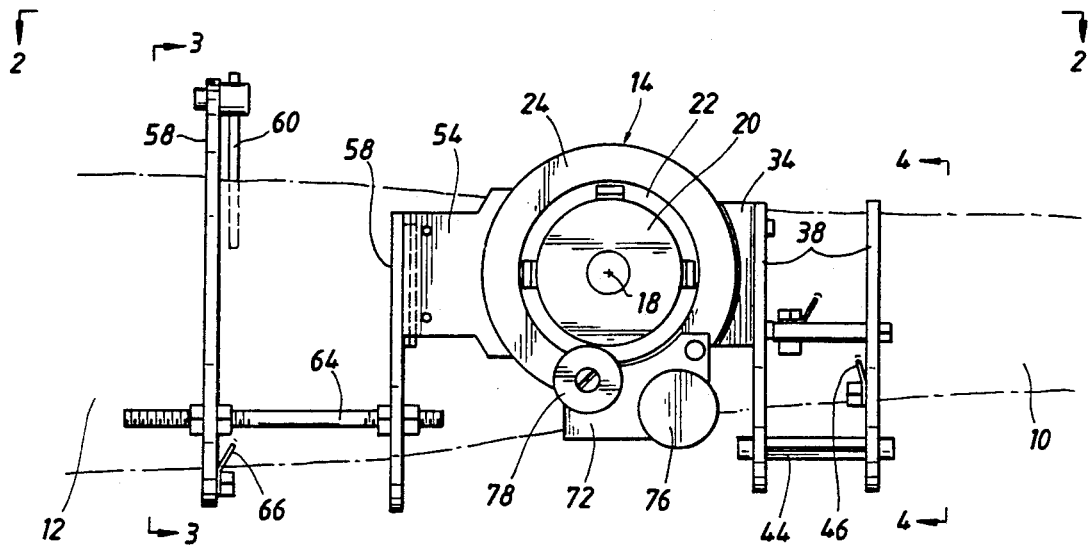
FIG. 1 is a side plan view of the dynamic elbow brace which is the subject of the present invention, as the brace would be connected to an arm of a patient in extension.
Figure 2:
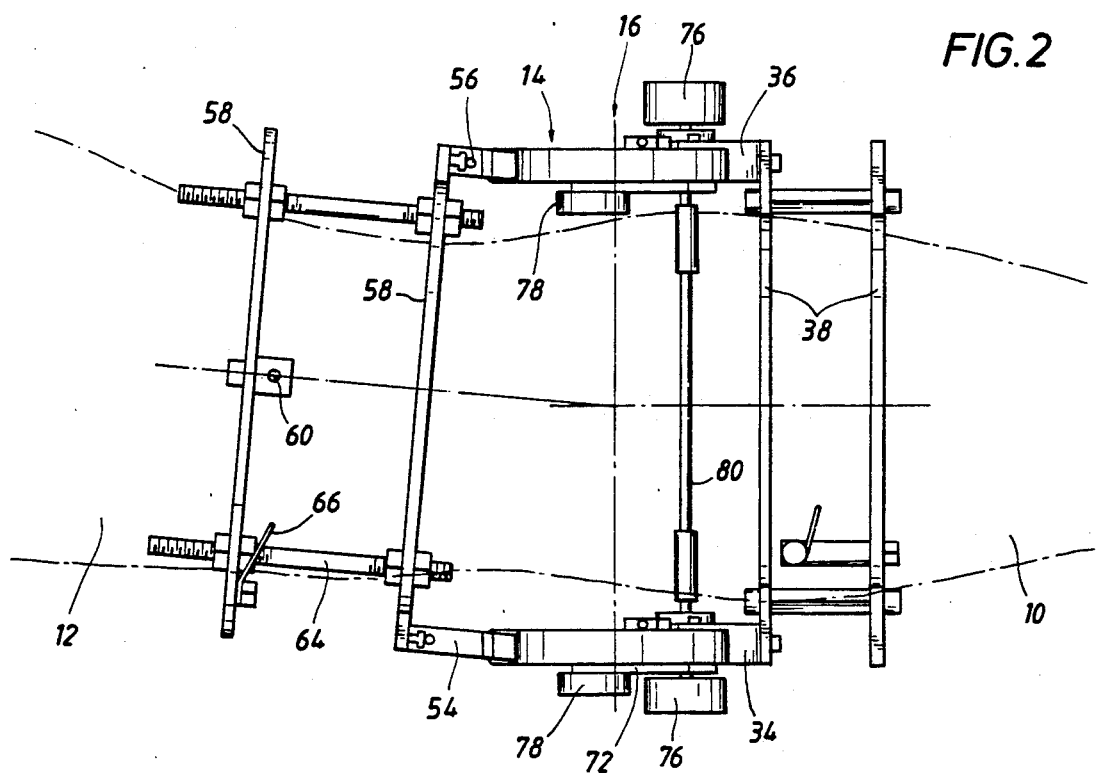
FIG. 2 is a bottom plan view of the dynamic elbow brace shown with a dashed line depiction of the axis of the underlying bones.

The dynamic joint support in a preferred embodiment of the present invention is shown as it would be connected to the arm of a patient in FIGS. 1 and 2, where reference numeral 10 identifies dashed lines illustrating the forearm of the patient and 12 the upper arm. The support includes a pair of hinges 14 which are collinear or aligned with the kinematic axis of the elbow as shown by center line 16 (see FIG. 2). This alignment can be accomplished through the use of an X-ray machine (not shown) which can center the hinge through radio-opaque cross hairs 18 provided in a central window 20 formed in the hinge 14, which is transparent to X-rays.

Figure 6:
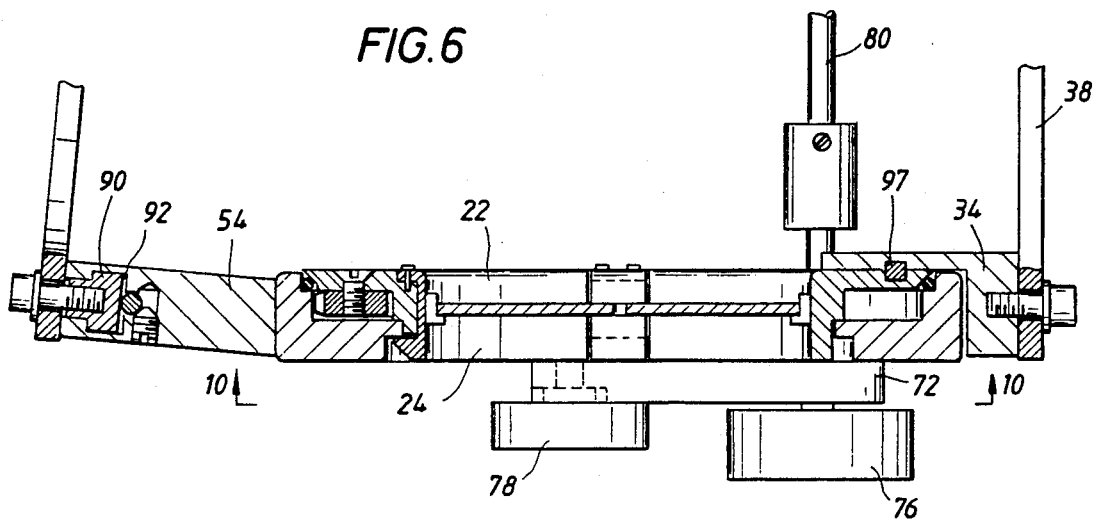
FIG. 6 is a top view of the proximal bracing section.
Figure 7:
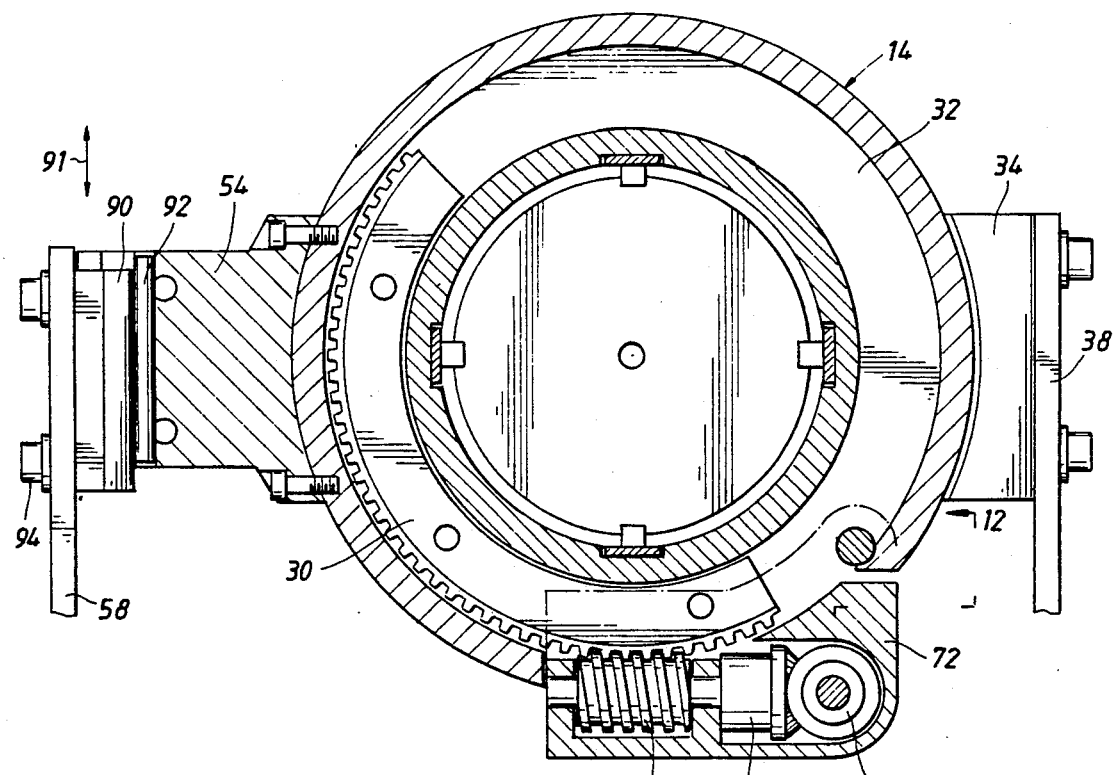
FIG. 7 is a side plan view partially in section of the hinge and the gear mechanism.
Figure 14:
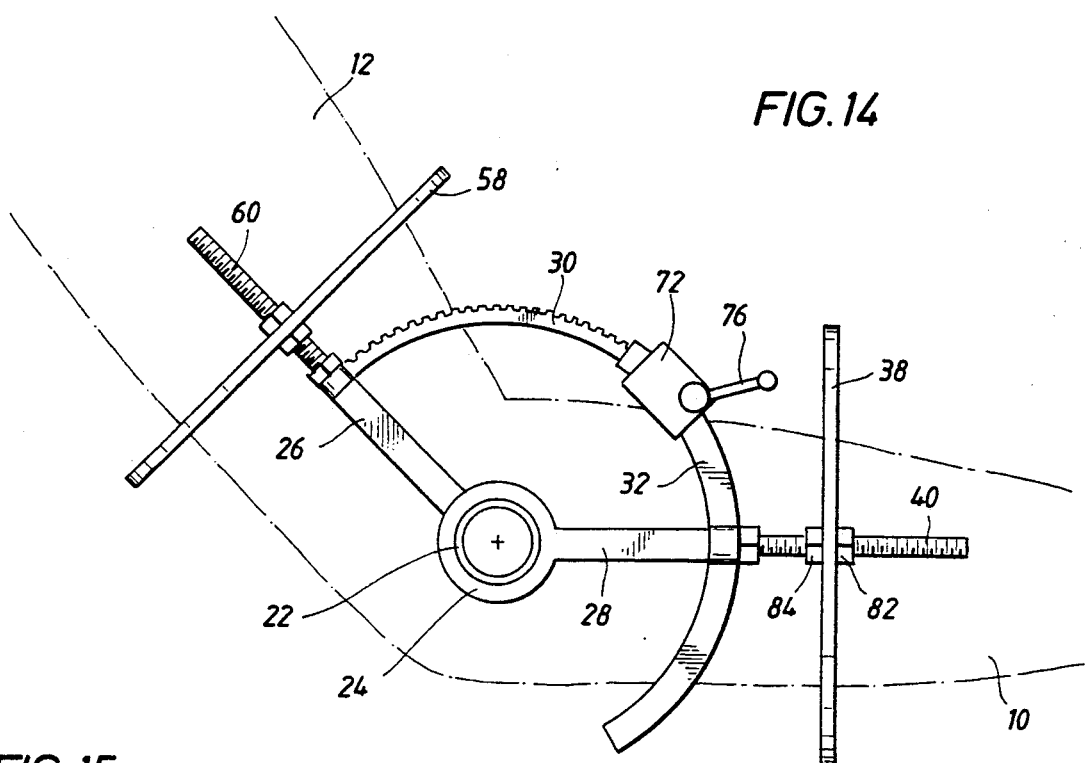
FIG. 14 is a side plan view of an alternative embodiment of the invention, as it would be attached to an arm in partial flexion.

Each hinge 14 includes a pair of fitted plates 22, 24 which are adapted to rotate relative to each other and are respectively connected to arcuate members 30, 32 (FIG. 7). The connection of the rotating plates 22, 24 to the arcuate members 30,32 may be direct, as shown in FIGS. 6 and 7, or indirect, through radially-extending arms 26, 28 as shown in FIG. 14.

Referring again to FIGS. 1 and 2, distal adjustment blocks 34, 36 connect the hinges 14 to one or more annular support rings 38. Alternatively, as shown in FIG. 15, the hinges 14 may be connected to one or more annular support rings 38 by threaded rods 40.

Figure 3:
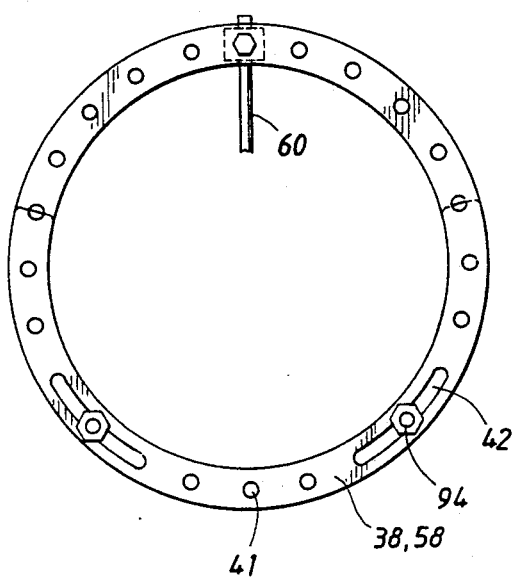
FIG. 3 is a partial plan view of a support ring, for fixing the support to the bone.
Figure 4:
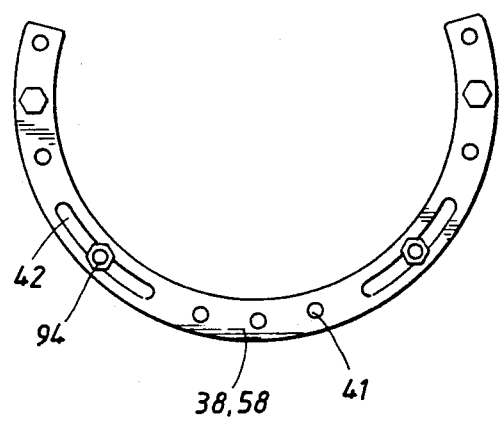
FIG. 4 is similar to FIG. 3, showing a support ring which only partially encircles the limb.

As shown in FIGS. 3 and 4, the annular support rings 38 may be formed in a closed or partial circle and contain a plurality of openings 41 around their circumference. The support rings 38, 58 can be similar to ones developed by Dr. Ilizarov for use in bone lengthening or rehabilitation techniques, which are commonly known as Ilizarov rings.

Rods 44 extend between the annular support rings 38 when more than one is used. Wires 46 or pins (not shown) attached to the annular support rings 38 or to the extending rods 44 are embedded in the ulna for holding the support ring 38 rigidly in place relative to the forearm 10. (While pins might likewise be placed in the radius, because of interference with the motions of supination and pronation, such placement is not preferred.)

Figure 15:
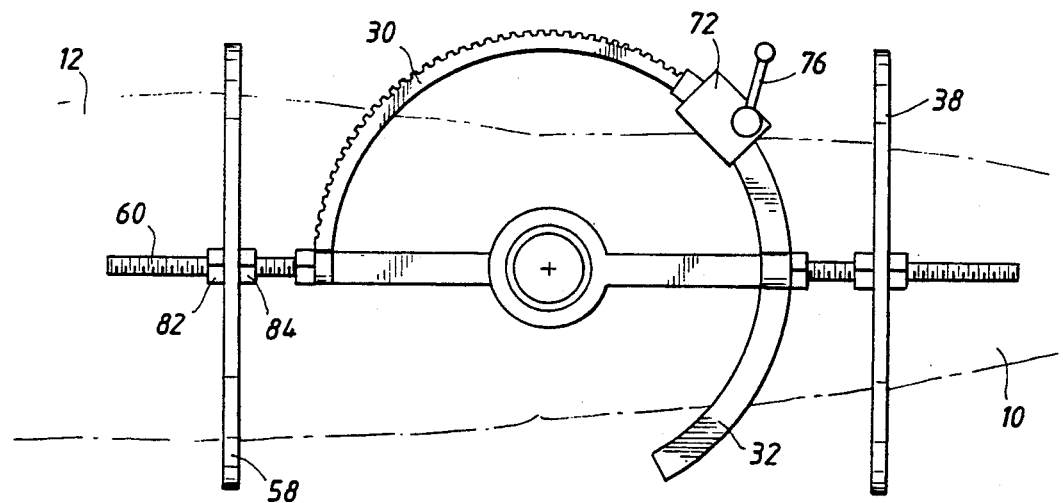
FIG. 15 is a similar view as FIG. 14, with the arm in extension.
Figure 16:
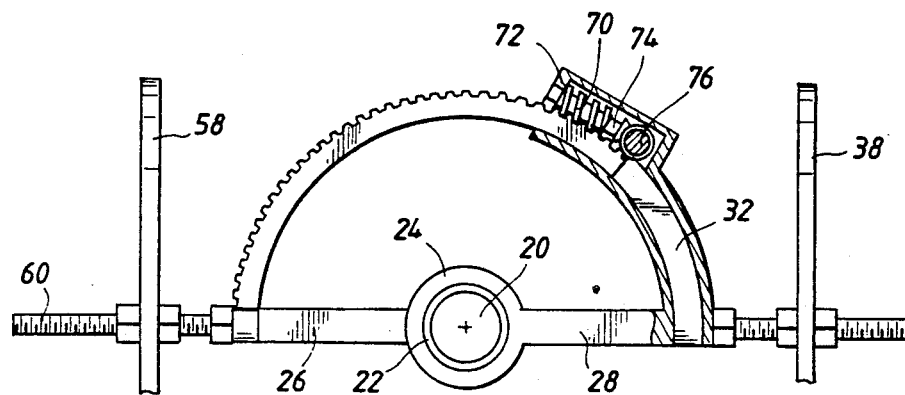
FIG. 16 is a side plan view partially in section showing the gear mechanism of the alternative embodiment.

Proximal adjustment blocks 54, 56 or rod 60 in the embodiment of FIGS. 14–16 likewise connect the hinges 14 to one or more annular support rings 58 which are connected to the humerus through a series of pins 60 or wires 66 which are in turn connected to the support rings 58 or through rods 64.

As shown in FIG. 2, the hinges 14 are located both medial and lateral to the elbow joint along with corresponding adjustment blocks 34, 36 and 54, 56. Also, arcuate members 30, 32 of the hinges 14 are located on both sides of the joint.

The hinges 14, the adjustment blocks 34, 36 and 54, 56, rods 44, 64 and the support rings 38, 58 form external bracing sections which can be connected to the respective bones in the forearm and upper arm. Through the hinges 14, these elements allow the arm of the patient to move between the extended position of FIG. 1, where the arm is relatively straight, and the flexed position of FIG. 5, where the forearm 10 and upper arm 12 are moved toward each other. As described in detail below, the bracing sections can be precisely aligned with the kinematic axis of the joint so that when the extension and flexion described above takes place, contractures are prevented, reduced or eliminated.

As shown best in FIG. 7, the arcuate member 30 is formed as a curved rack which mates with a worm 70 located in a housing 72 mounted on arcuate member 32. The housing 72 is hollow, to allow the curved rack 30 to telescope within the arcuate arm 32 as the worm 70 is moved through rotation of a miter gear 74. A crank 76 can be connected to the miter gear 74 which, when turned manually, will effect extension and flexion of the arm of the patient. Alternatively, a suitable connection can be provided for connecting a motor to the miter gear 74 for effecting continuous passive motion to the arm of the patient.

Figure 8:
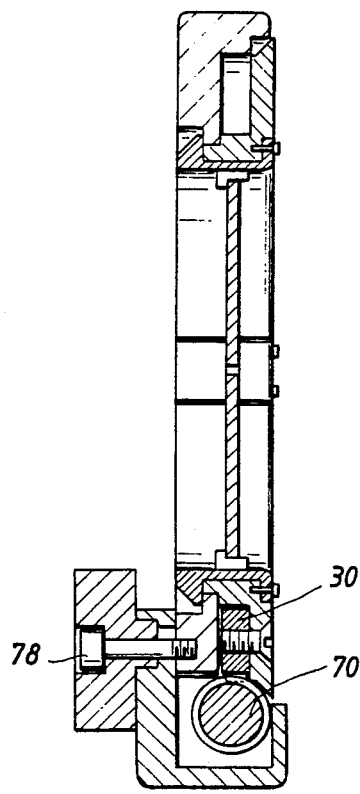
FIG. 8 is a top plan view partially in section showing the engaged clutch mechanism.
Figure 10:
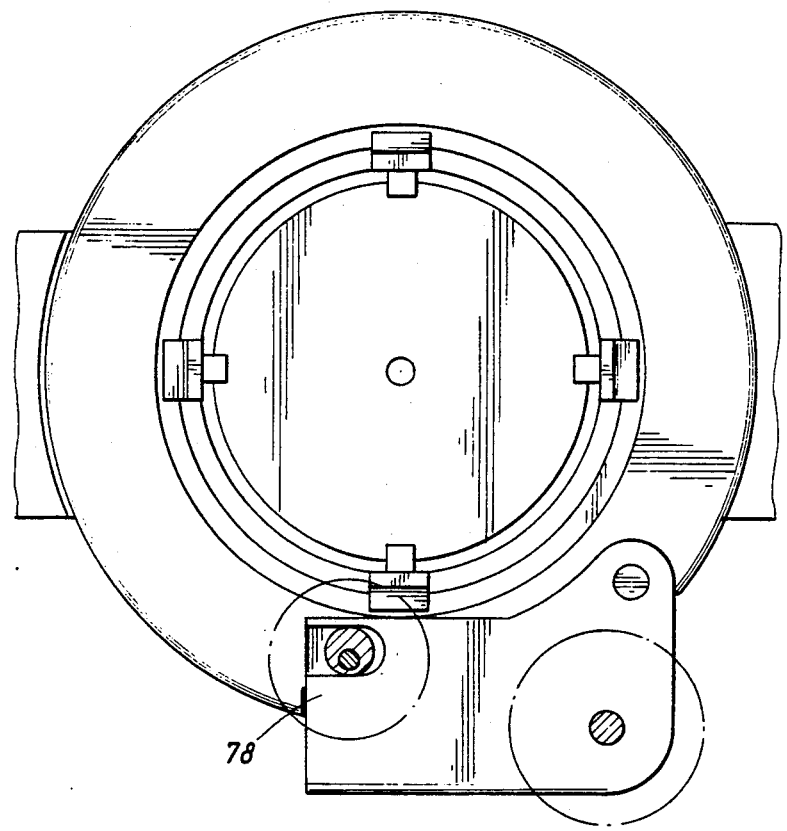
FIG. 10 is a perspective view of the hinge showing the clutch mechanism.
Figure 9:
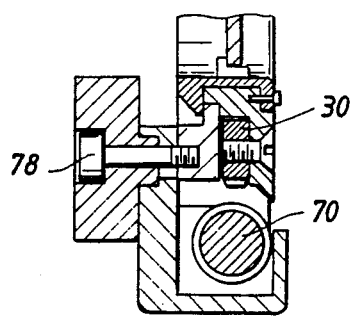
FIG. 9 is a top plan view partially in section showing the disengaged clutch mechanism.
Figure 11:
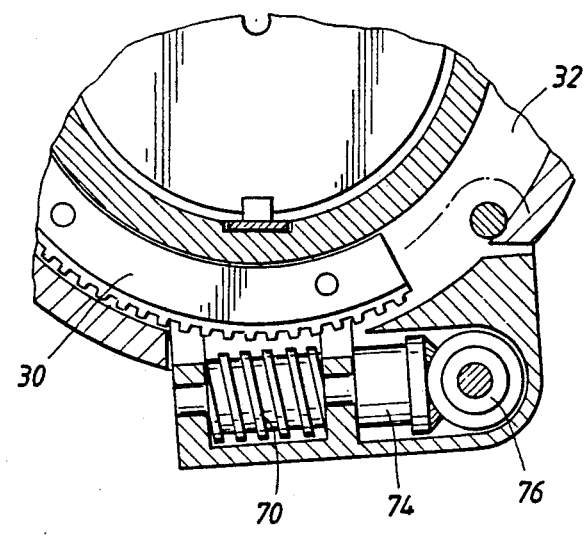
FIG. 11 is a sectional view of the disengaged gear mechanism.

Referring now to FIGS. 8 and 9, a clutch 78 can be provided for selectively disengaging the curved rack 30 from the worm mechanism 70 so that the patient can use his or her own power to extend or flex the arm. The clutch 78 may be for example, a set screw or crank which, when engaged, as showing in FIG. 8, causes the curved rack 30 to engage the worm 70. When the clutch 78 is disengaged, as shown in FIGS. 9 and 11, the curved rack 30 is disengaged from contact with the worm 70, and permits free movement of the arcuate members 30, 32 relative to each other.

Figure 12:
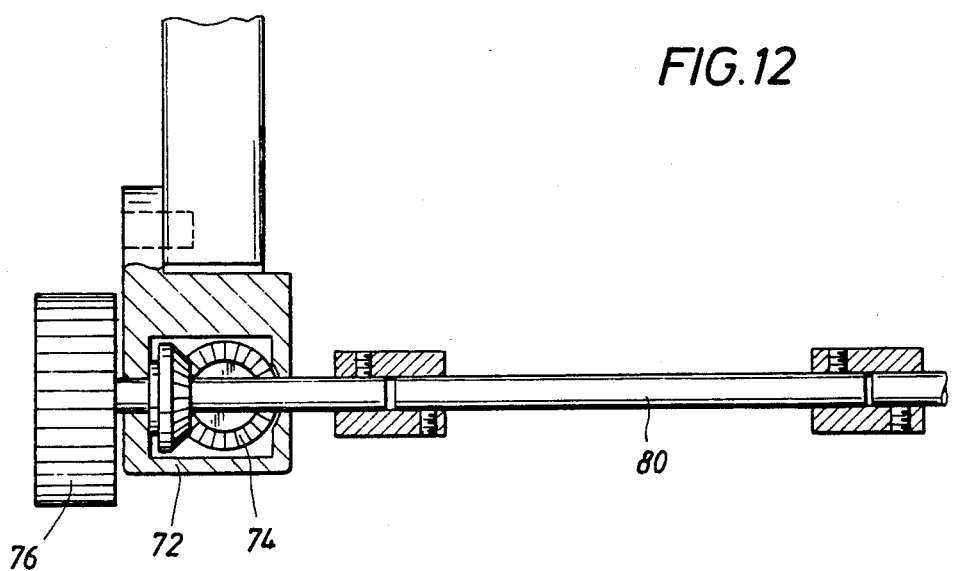
FIG. 12 is a plan view partially in section of the gear mechanism and the drive shaft.

The arcuate members 30, 32 on the opposing sides of the elbow joint can each move relative to each other as described above. Only one hinge of the two opposing hinges on each side of the joint requires the gearing mechanism as described. Referring to FIGS. 2 and 12, a drive shaft 80 is connected between the gear housing 72 of each hinge 14, and transfers rotational energy from one hinge to the opposite hinge. Turning of the crank 76 of one hinge thus drives each hinge in synchrony through the drive shaft 80.

The drive shaft 80 may extend between the hinges either anterior or posterior to the joint. Because of the incidence of anterior swelling in trauma to the elbow joint, it is generally preferred that the drive shaft 80 be positioned posterior to the elbow joint. For ease of patient use, it may be preferred that the crank be located on the medial aspect of the elbow joint.

While only one gear mechanism is required, it is preferred that both hinges 14 contain the complete gear system. Having the gear mechanism available on each side of the joint provides more accurate tracking of the arcuate members 30, 32, allows the device to be interchangeable between right and left arms, and also allows maximal flexibility of patient and physician use. In the preferred embodiment, turning of one crank 76 provides rotational energy to the drive shaft 80, which provides rotational energy to the miter gears 74 and worms 70 of both hinges in synchrony.

Figure 5:
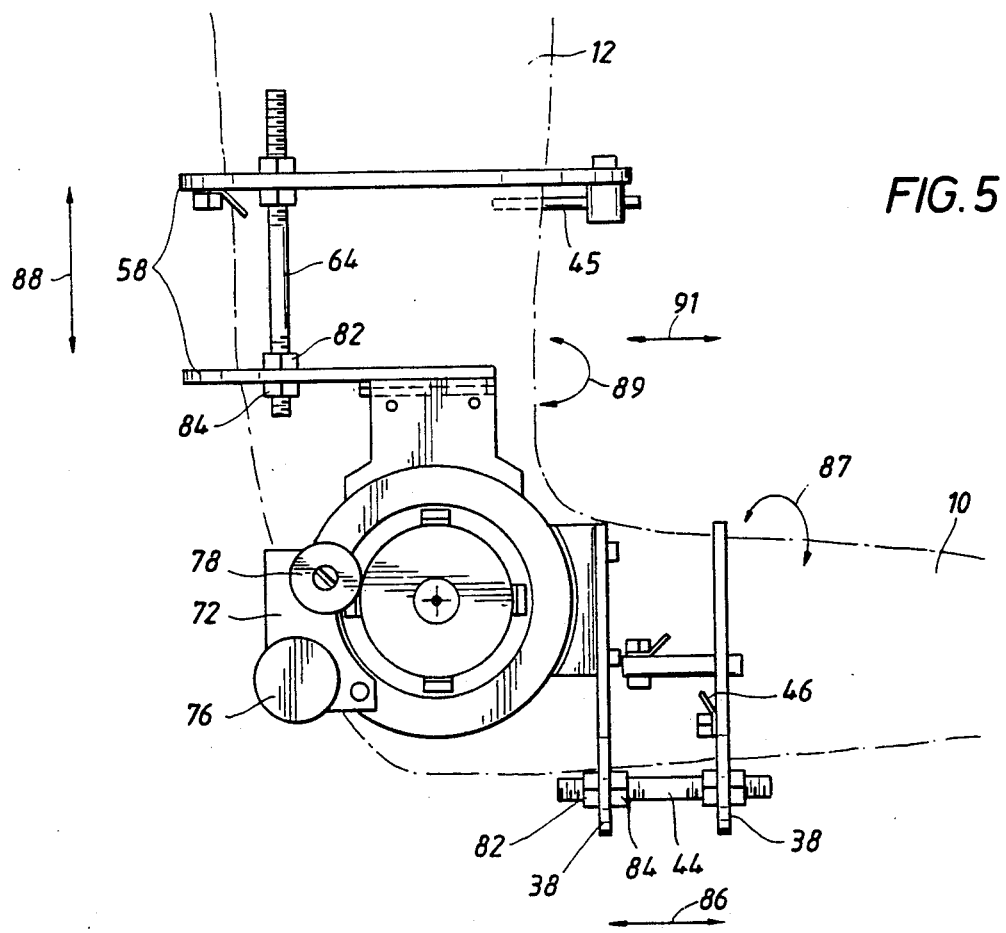
FIG. 5 is a side plan view of the dynamic elbow brace, as it would be connected to the arm of a patient in flexion.

Referring to FIG. 5, the dynamic support of the present invention is shown installed by first connecting the support rings 38, 58 to bones of the patient's arm using pins 45 or wires 46, with the remainder of the apparatus loosely connected and generally aligned. The proximal support ring 58 is oriented perpendicular to the proximal humerus of the arm 12, while the distal support ring 38 is oriented perpendicular to the ulna of the forearm 10. The extended rods 44, 64 are threaded with corresponding nuts 82, 84 so that the location of the hinge 14 can be adjusted in length relative to the support rings 38, 58 in the direction of arrows 86, 88.

As shown in FIGS. 3 and 4, openings 42 in the support rings 38, 58 are elongated so the hinge 14 can be adjusted circumferentially relative to the stabilized bone, as illustrated by arrows 87, 89 in FIG. 5. Rotational adjustments can be made as described above between the support ring 58 and the proximal adjustment blocks 54, 56 by way of the elongated slots 42 of the support ring 58. Once positioned rotationally, the support ring 58 is held tightly in place, for example, by tightening of screws 94 through the elongated slots 42 and into the adjustment block 54, 56.

The natural axis of the forearm of a patient 10 is offset from the axis of the upper arm 12 by approximately 7°. Proper alignment of the external support sections on opposite sides of the hinge is necessary in order to maintain the proper angle of the bones during extension and flexion. As shown in FIG. 2, to accommodate for this natural angle of the elbow joint, the lateral proximal adjustment block 54 is larger in size with respect to the medial proximal adjustment block 56. It is important that the variation in the medial and lateral blocks compensate for the 7° angle at the axis of the elbow joint.

It is contemplated that the device may be interchangeable between the right and left arms by exchanging the medial and lateral proximal adjustment blocks. It is also contemplated that proximal adjustment blocks of varied sizes may be substituted to compensate for variation in the distance between the hinges, for example, when treating a child versus an adult.

As shown in FIGS. 6 and 7, the proximal adjustment block 54, 56 includes a sliding block 90 and a track 92 in which the sliding block 90 slides to adjust the location of the hinge 14 in the anterior-posterior direction (arrow 91) relative to the proximal support ring 58 and thereby relative to the stabilized bone.

Figure 13:
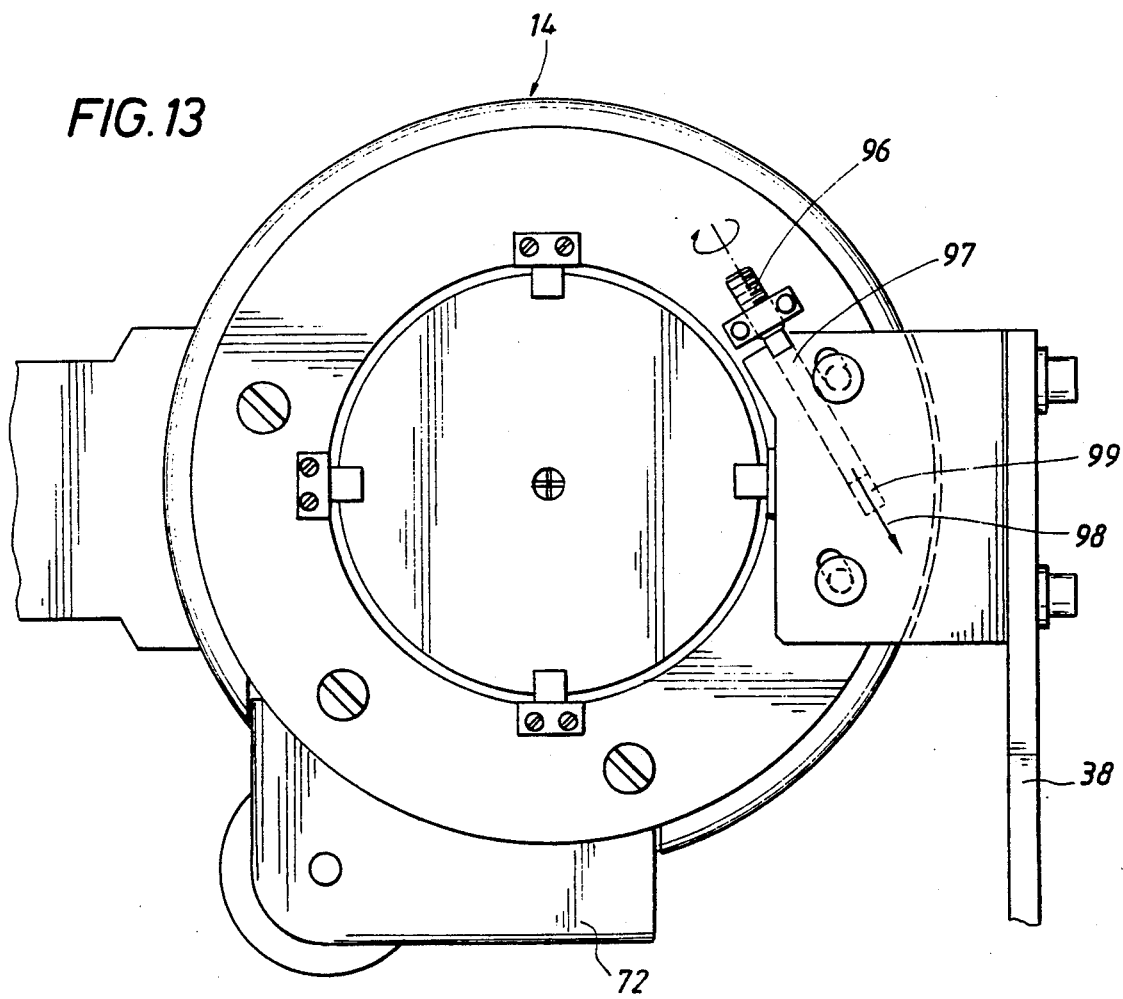
FIG. 13 is a side plan view of the hinge showing the distraction mechanism.

As shown in detail in FIG. 13, the distal support ring 38 is connected to the hinge 14 through the distal adjustment blocks 34, 36. When distraction of the joint is desired, the distal adjustment blocks 34, 36 allow the hinge 14 to be moved along a line about 30° relative to a line perpendicular to the bones of the forearm. This can be accomplished, for example, by turning a set screw 96 which moves a boss 97 in a track 99 to cause movement of the distal adjustment blocks 34, 36 along the line 98. This movement of the distal adjustment blocks allows the attached bones of the forearm to be distracted, or to be moved slightly out of contact with the humerus with the device, permitting motion of the joint during distraction. Distraction of the joint may be desired in treatment of injuries to the joint itself.

Through the mechanism described, the dynamic elbow support can be accurately aligned with the kinematic axis of the elbow through the use of an X-ray machine by aligning the cross hairs 18 in the X-ray transparent portions of the hinges 14. Fine adjustments can be made through the proximal and/or distal adjustment blocks 54, 56 and 34, 36. Once the dynamic elbow brace is accurately aligned in the preferred position, a patient can have his or her arm extended or flexed through the application of manual movement to the gearing mechanism or through connection to a motor for continuous passive movement. The clutch mechanism can be employed to disengage the curved rack from the worm so that the patient can actively move his or her arm through full extension and flexion.

The dynamic elbow brace of the present invention is useful in the treatment of trauma to the arm and forearm such as severe fractures, dislocations of the elbow and the like as well as the treatment of trauma to other joints where a high possibility of fracture and stiffness normally results from immobilization. The apparatus may be applied to the patient immediately to begin rehabilitation and prevent contracture. In some instances, it may be desirable to apply distraction to reduce the joint reaction force during flexion and extension. The dynamic brace allows for all of these treatments to occur through apparatus which is connected to bones on opposite sides of the joint distant from the joint so as not to interfere with movement and rehabilitation.

The dynamic joint brace of the present invention also permits readjustments as needed during therapy without significant interference using external adjustment mechanisms. Adjustments may be necessary if the patient should fall or otherwise disturb the set alignment during therapy. Alternatively, the device permits monitored therapy, with immediate and easily accomplished adjustments in the proper alignment. Adjustments may be made in rotation, anterior-posterior positioning, and distal-proximal positioning of the hinge relative to the fixed skeletal elements.

The dynamic joint brace of the present invention may be fabricated using materials known in the field. It is preferred that the materials used to fabricate the device permit sterilization of the device.

The foregoing description is considered to be illustrative and not limiting and variations and improvements to the invention can be made without departing from the spirit and scope of the invention. All such variations and improvements are contemplated as falling within the scope of the appended claims, which

I claim:

1. A dynamic support, comprising:
    proximal and distal external support sections, one for each skeletal element on opposite sides of a joint;
    connecting means for rigidly connecting each support section to a bone on its respective side of the joint, wherein said connecting means attaches to the bone at a distance from the joint and not at the axis of rotation of the joint;
    hinge means having an axis for connecting the support sections to each other in the vicinity of the joint so the hinge means will pivot the joint when the skeletal elements move through flexion and extension; and
    x-ray transparent means at the pivot point of the hinge means having radio-opaque indicia means for enabling alignment of the axis of the hinge means with the axis of the joint.

2. The dynamic joint support of claim 1, comprising:
    adjustment means for adjusting the position and orientation of the hinge relative to the respective support sections and relative to the axis of the joint.

3. The dynamic joint support of claim 1, wherein the hinge means includes a gear means for moving the support sections and consequently their respective skeletal elements through flexion and extensions in response to the application of external force to the gear means.

4. The dynamic joint support of claim 1, further comprising:
    distraction means for stably fixing bones of the joint out of contact with each other.

5. A dynamic joint support comprising:
    proximal and distal external support sections, one for each skeletal element on opposite sides of a joint;
    connecting means for rigidly connecting each support section to a bone on its respective side of the joint, wherein said connecting means attaches to the bone at a distance from the joint and not at the axis of rotation of the joint;
    hinge means for connecting the support sections to each other in the vicinity of the joint so the hinge means will pivot the joint when the skeletal elements move through flexion and extension, wherein the hinge means includes a gear means having two gear sections for moving the support sections and consequently their respective skeletal elements through flexion and extension in response to the application of external force to the gear means; and
    clutch means connected to said gear means for selectively engaging said gear sections such that the force is transferred between said gear sections to restrict free motion of the skeletal elements and permit controlled extension and flexion of the joint and for selectively disengaging the gear sections to allow the skeletal elements to move freely.

* * * * *